(12) United States Patent
Ashdown et al.

(10) Patent No.: US 11,470,703 B2
(45) Date of Patent: Oct. 11, 2022

(54) LIGHTING FOR ROOT GROWTH

(71) Applicant: SUNTRACKER TECHNOLOGIES LTD., Victoria (CA)

(72) Inventors: Ian Edward Ashdown, West Vancouver (CA); Wallace Jay Scott, Victoria (CA)

( * ) Notice: Subject to any disclaimer, the term of this patent is extended or adjusted under 35 U.S.C. 154(b) by 0 days.

(21) Appl. No.: 17/687,378

(22) Filed: Mar. 4, 2022

(65) Prior Publication Data

US 2022/0191993 A1  Jun. 16, 2022

Related U.S. Application Data

(63) Continuation of application No. 17/407,643, filed on Aug. 20, 2021, now Pat. No. 11,297,707, which is a
(Continued)

(51) Int. Cl.
*H05B 47/10* (2020.01)
*A01G 9/24* (2006.01)
(Continued)

(52) U.S. Cl.
CPC ............ *H05B 47/10* (2020.01); *A01G 7/045* (2013.01); *A01G 9/249* (2019.05); *A01K 29/00* (2013.01);
(Continued)

(58) Field of Classification Search
CPC . A01G 7/00; A01G 7/045; A01G 9/16; A01G 9/249; A01G 31/02; A01G 31/00; A01G 31/06; A01G 9/20; A01G 7/06; A01G 9/246; A01G 9/247; A01G 22/00; A01G 9/02; A01G 7/02; A01G 9/1438; A01G 22/15; A01G 31/04; A01G 9/14; A01G 9/26; A01G 31/047; A01G 9/24; A01G 9/023; A01G 7/04; A01G 13/0256; A01G 22/05; A01G 9/0297; A01G 2031/006; A01G 22/25; A01G 24/42; A01G 33/00; A01G 24/40; A01G 9/0293; A01G 9/18; A01G 22/60; A01G 24/10; A01G 24/28; A01G 24/23; A01G 24/25; A01G 27/003; A01G 31/045; A01G 9/143; A01G 27/00; A01G 31/042; A01G 24/44; A01G 29/00; A01G 9/029; A01G 2/20;
(Continued)

(56) References Cited

U.S. PATENT DOCUMENTS 9,974,243 B2 * 5/2018 Martin .................... A01G 9/249
2018/0007845 A1 * 1/2018 Martin .................... A01G 9/246

* cited by examiner

*Primary Examiner* — Monica C King

(57) ABSTRACT

A biological lighting system to provide temporally- and spatially-modulated photon flux output and spectral power distributions to plants on a circadian and circannual basis, or circadian and life cycle basis, to maximize effective and efficient growth in a horticultural setting. The photon flux or irradiance output and the spectral power distribution are modulated to match circadian and circannual rhythms, with individual or multiple luminaires controlled through one or more controllers. Different lighting spectra can be employed depending on the direction of illumination. The photon flux or irradiance output and the spectral power distribution may be set as best suited for any particular plant species, and the system is also useful for raising animals.

19 Claims, 5 Drawing Sheets

Related U.S. Application Data continuation of application No. 16/615,321, filed as application No. PCT/CA2018/050938 on Aug. 1, 2018, now Pat. No. 11,102,867.

(60) Provisional application No. 62/660,911, filed on Apr. 20, 2018, provisional application No. 62/647,650, filed on Mar. 24, 2018, provisional application No. 62/540,560, filed on Aug. 2, 2017.

(51) Int. Cl.
*H05B 47/11* (2020.01)
*A01G 7/04* (2006.01)
*A01K 29/00* (2006.01)
*A61M 21/02* (2006.01)
*A61M 21/00* (2006.01)

(52) U.S. Cl.
CPC ............. *A61M 21/02* (2013.01); *H05B 47/11* (2020.01); *A61M 2021/0044* (2013.01); *A61M 2205/587* (2013.01); *A61M 2250/00* (2013.01)

(58) Field of Classification Search
CPC ...... A01G 27/008; A01G 9/243; A01G 9/245; A01G 22/40; A01G 24/20; A01G 25/00; A01G 9/025; A01G 9/027; A01G 24/30; A01G 9/047; A01G 20/20; A01G 24/46; A01G 13/0268; A01G 22/30; A01G 9/12; A01G 13/0206; A01G 13/0225; A01G 13/06; A01G 2/00; A01G 22/20; A01G 22/22; A01G 25/167; A01G 27/005; A01G 9/022; A01G 9/22; A01G 2/10; A01G 22/35; A01G 24/22; A01G 24/35; A01G 25/09; A01G 25/165; A01G 27/02; A01G 9/1423; A01G 13/0237; A01G 13/0275; A01G 18/10; A01G 22/67; A01G 24/00; A01G 27/001; A01G 27/006; A01G 27/06; A01G 9/0299; A01G 9/083; A01G 9/088; A01G 9/1407; H05B 45/20; H05B 45/22; H05B 31/50; H05B 47/11; H05B 47/16; H05B 47/105; H05B 47/115; H05B 45/24; H05B 47/10; H05B 47/175; Y02A 40/25; Y02A 40/254; F24F 11/30; F24F 11/47; F24F 2120/10; F24F 2130/20; F24S 2201/00; G06F 30/20; G06F 17/11; G06F 30/13; G06F 2119/06; G06F 30/23; G06F 30/3323; G06F 2111/10; G05B 15/02; G05B 19/042; G05B 2219/2642; G05B 19/0426; G05B 19/048; G05B 2219/2639; G05B 13/048; G05B 13/0265
See application file for complete search history.

LIGHTING FOR ROOT GROWTH

TECHNICAL FIELD

The subject matter of the present invention relates to the field of biological lighting systems and more particularly, is concerned with providing temporally- and spatially-modulated spectral power distributions to plants and animals on a circadian basis to entrain circadian rhythms, and also on a circannual or life cycle basis.

BACKGROUND

Biologists have long known that plants and animals have both circadian and circannual rhythms, wherein their biological functions vary on a daily and annual basis. These rhythms are endogenously generated and self-sustaining, so that they persist in the absence of environmental time cues, or "zeitgebers." Flowering plants are obvious examples, as most flowers open or close at dawn and dusk. An example that demonstrates the self-sustaining nature of circadian rhythms is the sensitive heliotrope plant *Mimosa pudica*, whose leaves droop at night, even when the plant is kept in constant darkness. In animals, sleep is the most obvious example of circadian rhythms, but there are many more, including cardiovascular efficiency, blood pressure, bowel movements, alertness, and appetite.

There are similarly many other biological functions in plants that exhibit circadian rhythms, including leaf and flower movement, and nectar secretion (McClung, C. R., 2001, "Circadian Rhythms in Plants," *Annual Review of Plant Physiology* 52:139-162). More subtly, biochemical changes at the cellular level occur that prepare the plants for colder temperatures at night, regulate the opening and closing of stomata for gas exchange, anticipate possible infection by pathogens, produce wax to prevent water loss, and synthesize molecules that will remove reactive oxygen species before sunrise and protect against excess sunlight during the day. Kamioka, M. et al., 2016, "Direct Repression of Evening Genes by CIRCADIAN CLOCK-ASSOCIATED 1 in the Arabidopsis Circadian Clock," *The Plant Cell* 28:696-711 demonstrated that daily gene expression often occurs hours in advance, and in highly complex biochemical pathways, that control various mechanisms needed for plant health and survival.

Plants also exhibit circannual rhythms, obvious examples being the loss of leaves for deciduous trees in the autumn and annual tree ring growth. (Like mammals, reptiles, and amphibians living in colder temperature climates, trees and perennial plants hibernate during the winter months.) More subtly, flowering plants in temperate climates are influenced by the day length. So-called "short-day" plants flower when the night length ("skotoperiod") exceeds their critical "photoperiod," while "long-day" plants flower when the skotoperiod is less than their critical photoperiod. (Some "day-neutral" flowering plants rely on other environmental cues, such as periods of low temperature.)

Plants rely on photoreceptor proteins ("photopigments") such as phytochromes (which are sensitive to red light) to determine the night length and so initiate flowering at the appropriate time (e.g., Smith, H., 2000, "Phytochromes and Light Signal Perception by Plants—An Emerging Synthesis," *Nature* 407:585-591). The roles of these photopigments are ascertained by breeding genetically-modified plants in which the genes responsible for the biosynthesis of the photopigments are not expressed. Floriculturists use both incandescent lamps and, more recently, red light-emitting diodes (LEDs) to influence seed germination, leaf development, and stem elongation, and to promote or suppress flowering in photoperiodic plants. This is possible because the role of phytochromes has been well understood for many decades, and the plant responses are clearly evident.

Generally assuming that photopigments such as phytochromes are alone responsible for photoperiodic responses, horticultural research has to date focused on the photon flux delivered to plants on a daily basis. This is the basis of the "daily light integral" (DLI), which is measured as moles of photons received per square meter in a 24-hour period. Horticulturalists have documented the daily light integrals of most economically-important crops and use this information to determine the suitability of various climatic regions for their production. (Circannual rhythms are accounted for by "growing degree-days," a metric that is based on ambient temperature rather than available daylight.)

The daily light integral as a metric for predicting plant growth is, however, perhaps overly simplistic. As described by Blanchard, M. G. and E. S. Runkle, 2016, "Investigating Reciprocity of Intensity and Duration of Photoperiodic Lighting to Regulate Flowering of Long-Day Plants," *Acta Horticulturae* 1134:41-48, the relationship between the photon flux density at the plant canopy (measured in micromoles per square meter per second, or $\mu mol/m^2$-sec) and the duty factor of the cyclic exposure (e.g., 2 minutes every 45 minutes versus continuous exposure) is not necessarily linear—it depends on the plant species.

Central then to both the circadian and circannual rhythms of plants is the reliable functioning of the endogenous circadian clocks. Without daily environmental cues, the free-running circadian clock periods are typically less than 24 hours (McClung 2001.) As shown by Dodd, A. N., et al., 2005, "Plant Circadian Clocks Increase Photosynthesis, Growth, Survival, and Competitive Advantage," *Science* 309:630-633, plants with entrained circadian rhythms contain more chlorophyll, fix more carbon, grow faster, and survive better. Similarly, many studies have shown that circadian rhythm disruption in animals—"jet lag" in humans is a good example—negatively impact the animals' long-term health and well-being. It is important then to understand the environmental cues that serve to entrain both circadian and circannual rhythms to their daily and annual periods respectively.

Circadian Rhythm Entrainment

In Walmsley, L., et al., 2015, "Colour as a Signal for Entraining the Mammalian Circadian Clock," *PLOS Biology* 13(4):e1002127, the researchers investigated the entrainment of circadian and circannual rhythms in wild mice. They noted that daylight irradiance may not be the most reliable zeitgeber for entraining their circadian and circannual rhythms. In particular, the daylight irradiance may vary markedly and rapidly from minute to minute and day to day, depending on the cloud cover. The average daylight colour, however, is remarkably constant from day to day. (As noted in Lee, R. L., and J. Hernández-Andrés, 2006, "Colour of the Daytime Overcast Sky," *Applied Optics* 44(27):5712-5722, clouds diffuse daylight, but rarely change its average colour, expressed as correlated colour temperature. The colour further varies only slowly throughout most of the day, apart from dawn and dusk.) As reported by Walmsley et al. (2015), the ratio of yellow to blue light, or what they refer to as "relative colour," varies much less than daylight irradiance (FIG. 1). They demonstrated that, at least for wild mice, circadian rhythm entrainment is most likely due to changes in the average sky colour at dawn and dusk, rather than changes in daylight irradiance.

Walmsley et al. (2015) also reported that the ratio of yellow to blue light consistently varies by a factor of three over a period of 30 minutes at dawn and dusk, regardless of whether the sky condition is clear or overcast (FIG. 2). Brown, T. M., 2016, "Using Light to Tell the Time of Day: Sensory Coding in the Mammalian Circadian Visual Network," *Journal of Experimental Biology* 219:1779-1792, similarly reported marked changes in the spectral power distribution of daylight between a solar inclination of six degrees before and after sunset (FIG. 3).

Brown (2016) further noted that fish, reptiles, and possibly birds have the ability to distinguish colour with their pineal and parietal organs. Even some plankton, such as dinoflagellates, rely on colour to entrain their circadian rhythms, using rhodopsin, chlorophyll, and another unknown photopigment (Roenneberg, R., and R. G. Foster., 1997, "Twilight Times: Light and the Circadian Rhythms," *Photochemistry and Photobiology* 66(5):549-562).

Another example was reported by Sweeney, A. M. et al., 2011, "Twilight Spectral Dynamics and the Coral Reef Invertebrate Spawning Response," *Journal of Experimental Biology* 214:770-777, wherein the circannual synchronized spawning of corals is determined primarily by shifts in twilight colour and irradiance on nights immediately before and after the full moon.

Given these examples and more (e.g., Brown 2016), it is evident that changes in daylight colour during twilight are an important zeitgeber for entraining both circadian and circannual rhythms across the animal kingdom.

Data Fusion

Data fusion is the process of integrating multiple data sources to produce more consistent, accurate, and useful information than that provided by any individual data source. While Walmsley et al. (2015) concluded that wild mice use daylight colour rather than irradiance to entrain their circadian rhythms, it is more likely that the mice instead combine the two input signals, as shown in FIG. 1. In terms of phase-locked loop design (wherein circadian rhythms are seen as biological oscillators—see Rascher, U. et al., 2001, "Spatiotemporal Variation of Metabolism in a Plant Circadian Rhythm: The Biological Clock as an Assembly of Coupled Individual Oscillators," PNAS 98(20): 11801-11805), a sudden but consistent periodic pulse at dawn and dusk is better for entrainment than a randomly variable and noisy signal such as varying daylight irradiance.

Brown (2016) and others have further reported that animals use a "temporal gating mechanism" for photoreceptors, wherein the response to inputs from non-imaging photoreceptors (intrinsically photosensitive retinal ganglion cells, or ipRGCs, in the human retina) varies depending on the time of day. The purpose of this gating mechanism appears to be to maximize sensitivity to changes in both daylight colour and irradiance at sunrise and sunset, while ignoring such changes during the day. In other words, the input signals are temporally preconditioned to maximize their usefulness in synchronizing the phase-lock loop performance of the circadian clocks.

Plants appear to have a similar gating mechanism, wherein they are sensitive to changes in red light at sunset and blue light at sunrise (e.g., Hanyu, H., and K. Shoji, 2002, "Acceleration of Growth in Spinach by Short-term Exposure to Red and Blue Light at the Beginning and at the End of the Daily Dark Period," *Acta Horticulturae* 580:145-150 and Ohashi-Kaneko, et al., 2010, "Low-light Irradiation at the Beginning or the End of the Daily Dark Period Accelerates Leaf Expansion and Growth in *Spinacia oleracea* L.", *Environmental Control in Biology* 48(4): 161-173).

It is further well known that plants synchronize their circadian clocks in response changes in the ratio of red to far-red light (R:FR) at the end of the day (e.g., Demotes-Mainard, S., et al., 2016, "Plant Responses to Red and Far-red Light, Applications in Horticulture," *Environmental and Experimental Botany* 121:4-21). The R:FR ratio of direct sunlight is about 1.3 during most of the day, but it approaches 0.6 or so during twilight. Each phytochrome molecule has two states called "isoforms." Left in the dark for several hours, it reverts to a state called $P_r$, where it strongly absorbs red light. If a phytochrome molecule in this state absorbs a red photon, it changes to its $P_{fr}$ state, where it absorbs far-red radiation. If the molecule absorbs a far-red photon, it reverts back to its $P_r$ state. When in its $P_{fr}$ state, the molecule is biologically active, and may interact with the plant's molecular machinery. Given this, phytochrome can be seen as a reversible biological switch that can enable or inhibit various plant functions. The R:FR ratio is thus another circadian zeitgeber, one that is commonly used by floriculturists to advance or delay flowering by irradiating the plants at night ("night lighting") to disrupt their circadian rhythms.

As might be expected with phase-lock loops, electric light pulses presented to animals shortly before dawn may advance the circadian clock phase, while electric light pulses shortly after dusk may delay the clock phase. If the biological clock's intrinsic period is shorter than 24 hours, the animal will primarily use dusk light for entrainment. If, on the other hand, the intrinsic period is longer than 24 hours, the animal will primarily use dawn light for entrainment.

Referring to plants, McClung (2001) noted that plants use both light and temperature as input signals for circadian rhythm entrainment, and likely perform data fusion on these signals to obtain a statistically more significant entrainment signal for circadian and circannual rhythms. Although not discussed by McClung or others, annually-varying environmental conditions such as soil moisture content, soil acidity, salt content, nutrient availability, carbon dioxide concentration (in enclosed greenhouses and vertical farms), and wind may also be involved in circannual rhythm entrainment.

Plant Photoreceptors

Plants cannot, of course, "see" colour in the sense that animals, and particularly mammals, can. The human visual system, for example, relies on opsins, including rhodopsin, melanopsin, and possibly neuropsin (Brown 2016), with colour vision conferred by the opsins OPN1LW, OPN1MW, and OPN1SW (e.g., Terakita, A., 2005, "The Opsins," *Genome Biology* 6:213). Wild mice have similar but not identical opsins that are sensitive to yellow light and ultraviolet radiation (Walmsley et al. 2015).

While plants may not "see" in the sense of visual images, they are nonetheless capable of sensing the colour of daylight and electric lighting due to the spectral absorbance characteristics of various known classes of plant photoreceptors (e.g., Briggs, W. R., and M. A. Olney, 2001, "Photoreceptors in Plant Photomorphogensis to Date. Five Phytochromes, Two Cryptochromes, One Phototropin, and One Superchrome," *Plant Physiology* 125:85-88): phytochromes (red light), cryptochromes (blue light), phototropins (blue light), UVR8 (ultraviolet radiation), and cryptochromes (blue light). Thus, while plants may not see colour in any visual sense, they are certainly capable of sensing differences in the spectral power distribution of daylight and electric lighting that we may perceive as different colours.

Infrared Radiation

As noted in ASABE, 2016, "ANSI/ASABE S640: Quantities and Units of Electromagnetic Radiation for Plants (Photosynthetic Organisms)," American Society of Agricultural and Biological Engineers and elsewhere, the spectral wavelengths that plant photoreceptors are capable of sensing range from 280 nm (ultraviolet-B radiation) to 800 nm (far-red light). However, as reported by Johnson, C. F. et al., 1996, "Infrared Light-emitting Diode Radiation Causes Gravitropic and Morphological Effects in Dark-Grown Oat Seedlings," *Photochemistry and Photobiology* 63(2):238-242, plants also appear to be capable of sensing and responding to near-infrared radiation at approximately 880 nm and 935 nm.

A possible photoreceptor for near-infrared radiation is cytochrome c oxidase, which is a protein complex found in the mitochondria of all eukaryotes. It is a terminal enzyme of the respiratory chain, regulating the transfer of electrons from cytochrome to molecular oxygen. As reported by Karu, T., 2010, "Multiple Roles of Cytochrome c Oxidase in Mammalian Cells Under Action of Red and IR-A Radiation," *Life* 62(8):607-610, cytochrome C in mammalian cells has a peak in its action spectrum at 825 nm. By coincidence, the high-pressure sodium (HPS) lamps often used for supplemental electric lighting in greenhouses and poultry farms have a strong spectral peak at 820 nm (FIG. 4).

Karu (2010) discusses the effects of near-infrared radiation (IR-A) on mammalian, and in particularly human, cells. He notes in particular that exposure to IR-A radiation at sunrise may precondition dermal fibroblasts against damage by exposure to ultraviolet radiation during the day. While this cannot be regarded as definitive evidence for plants, cytochrome c oxidase is nonetheless present in the mitochondria of all plants (e.g., Dahan, J., et al., 2014, "Disruption of the CYTOCHROME C OXIDASE DEFICIENT1 Gene Leads to Cytochrome c Oxidase Depletion and Reorchestrated Respiratory Metabolism in Arabidopsis," *Plant Physiology* 166:1788-1802).

This is important because as reported by Poyton, R. O. and K. A. Ball, 2011, "Therapeutic Photobiomodulation: Nitric Oxide and a Novel Function of Mitochondrial Cytochrome C Oxidase," *Discovery Medicine* 11(57):154-159, exposure to low-level intensity light (albeit at 590 nm for human subjects) enhances nitric oxide (NO) synthesis by cytochrome c oxidase without altering its ability to reduce oxygen. Nitric oxide, according to Rio, L. A. et al., 2004, "Nitric Oxide and Nitric Oxide Synthase Activity in Plants," *Phytochemistry* 65:783-792, functions as an intracellular and intercellular signaling molecule in plants. As reported by Beligni, M. V. and L. Lamattina, 2001, "Nitric Oxide in Plants: The History is Just Beginning," *Plant, Cell and Environment* 24:267-278, exogenously-applied NO results in increased leaf expansion rates, stem and root elongation, delayed senescence, accelerated seed germination, and increased post-harvest life of flowers, fruits, and vegetables.

Anecdotal reports from horticulturalists have indicated that cucumbers, tomatoes, and gerbera (African daisies) do not grow as well under LED-based lighting as they do under HPS lighting, even with comparable photosynthetically active radiation (PAR) values. It is therefore proposed that the difference is the lack of 820 nm radiation with LED-based lighting, and that horticultural luminaires equipped with near-infrared LEDs with peak wavelengths between approximately 800 nm and 1000 nm, and which provide irradiance levels comparable to HPS lighting, will result in better plant health and growth.

It is also possible, based on the evidence of the response of human skin to near-infrared radiation at dawn to precondition the skin against ultraviolet radiation damage later in the day (Karu 2010), that a similar cellular mechanism exists in plants, which are also susceptible to ultraviolet radiation damage of their leaves, stems, and flowers. As such, horticultural luminaires equipped with near-infrared LEDs with peak wavelengths would provide benefits to plants grown in greenhouses with supplemental lighting.

Directionality Sensing

It has been hypothesized that plants may be able to image their environment using ocelli, or photosensitive "eye spots." Baluŝka, F., and S. Mancuso, 2016, "Vision in Plants via Plant-Specific Ocelli?", *Trends in Plant Science* 21(9): 727-730, for example, noted that the upper epidermal cells of many leaves are shaped like convex or planoconvex lenses, which in turn are capable of focusing light on the photosensitive subepidermal cells. This hypothesis was recently supported by Crepy, M. A. et al., 2015, "Photoreceptor-mediated Kin Recognition in Plants," *New Phytologist* 205:329-338, wherein *Arabidopsis thalania* plants were shown to visually recognize plant kin and modify their growth accordingly.

Further evidence in support of this hypothesis comes from Hayakawa, S. et al., 2015, "Function and Evolutionary Origin of Unicellular Camera-Type Eye Structure," *PLoS One* 10(3):e0228415, who reported that ocelloids in the dinoflagellate family Warnowiacease function as primitive eyes, enabling the plankton to sense and swim towards daylight in order to maximize photosynthesis opportunities. Schuergers, N. et al., 2016, "Cyanobacteria Use Microoptics to Sense Light Direction," *eLife* 5:e12620 reported similar capabilities for even simpler life forms, suggesting that primitive vision capabilities are not limited to animals.

While apparently not considered in the literature, it is possible that plant leaves may function as compound lenses similar to those evolved by insects and crustaceans. Given that most leaves move in the wind, any perceived image would have very low resolution. However, this may be sufficient to determine, for example, the directionality of direct sunlight or the spatial distribution of sky colour at sunrise and sunset. (An example of this from the animal kingdom is presented in Sumner-Rooney, L. et al., 2018, "Whole-body Photoreceptor Networks are Independent of 'Lenses' in Brittle Stars," Proc. Royal Society B 285(1871), wherein photoreceptor cells embedded in skin across the entire body of brittle stars enables them to perceive distant shadows and so avoid potential predators.)

The sky colour on clear days near sunrise and sunset is typically different than the average sky colour, due to Rayleigh scattering of blue light and ozone absorption of red light by the atmosphere (e.g., Hulburt, E. O., 1953, "Explanation of the Brightness and Colour of the Sky, Particularly the Twilight Sky," *Journal of the Optical Society of America* 43(2):113-118). More important, however, is the spatial difference in sky colour at sunset and twilight, varying from yellow and red near the horizon to blue at zenith. It is therefore reasonable to hypothesize that plants perceive the directionality of red and blue light at dawn and dusk and use data fusion to extract a more reliable zeitgeber for circadian rhythm entrainment than relying on daylight colour and irradiance alone.

It is also possible that rather than relying on putative ocelli, plants perceive changes in red light using red-sensitive phytochromes and changes in blue light using blue-sensitive cryptochromes and/or phototropins. As reported by Liscum et al., 2014, "Phototropism: Growing Towards an Understanding of Plant Movement," *The Plant Cell* 26:38-55, plants such as sunflowers follow the path of the sun during the day using phototropins phot1 and phot2, which signal stem cells to grow and so turn the flowers in the direction of the sun. It is known that these photoreceptors mediate a number of other plant functions in response to blue light, including stomatal opening, photosynthetic gas exchange, as well as cotyledon and leaf blade expansion, flattening, and positioning. It is therefore reasonable to assume that the phototropin signals (and possibly those from cryptochromes) would be used with the phytochrome signals for data fusion.

Whatever the underlying mechanism, plants appear to be capable of sensing the spatial and temporal distribution of both the spectral power distribution (i.e., colour) and irradiance of daylight across the sky dome at dawn and dusk. (It is also conceivable that plants may be able to sense the polarization of daylight.) This suggests at least eight co-dependent zeitgebers: the vertical distribution of colour and irradiance from horizon to zenith, the horizontal distribution of colour and irradiance from the solar to antisolar positions, and their temporal changes, that may be combined using data fusion. As proposed by for example Trewavas, A., 2003, "Aspects of Plant Intelligence," Annals of Botany 92:1-20, such capabilities may be reasonably expected of higher plants.

Root Growth

As reported by Mo, M. et al., 2015, "How and Why Do Root Apices Sense Light Under the Soil Surface?", *Frontiers in Plant Science* Vol. 6, Art. 775, plant roots have photoreceptors that sense daylight penetrating up to several millimeters below the surface. These photoreceptors include UVR8, cryptochromes, phototropins, and phytochromes, even though red and far-red light penetrates more deeply than blue light and ultraviolet radiation.

Christiaens, A. et al., 2016, "Light Quality and Adventitious Rooting: A Mini-Review," *Acta Horticulturae* 1134: 385-394, surveyed 18 papers on trial-and-error studies of in vitro plant cultures to determine the effects of broadband and quasimonochromatic visible light on root growth. Other studies have elucidated the role of red and far-red light (e.g., Correll, M. J., et al., 2005, "The Role of Phytochromes in Elongation and Gravitropism of Roots," *Plant Cell Physiology* 46(2):317-323) and blue light (e.g., Kutschera, U., et al., 2012, "Root Phototropism: From Dogma to the Mechanism of Blue Light Perception," *Planta* 235:443-452) in terms of photoreceptors and auxin signaling but did not consider the in vivo responses of plants in the field to natural daylight.

In addition to sensing scattered light within the soil, Lee, H.-J. et al., 2106, "Stem-piped Light Activates Phytochrome B to Trigger Light Responses in *Arabidopsis thalania* Roots," *Science Signalling* 9(452):ra106, demonstrated that ambient light incident upon plant leaves and stems is transmitted to the roots via vascular bundles. The photoreceptors in the roots are therefore potentially responsive to daylight colour changes, including those at dawn and dusk.

As reported in a survey by Satbhai, S. et al., 2015, "Underground Tuning: Quantitative Regulation of Root Growth," *Journal of Experimental Botany* 66(4):1099-1112, the spectral power distribution of above-ground irradiation can influence root growth rate, branching, and hair density, which may be particularly important when plants are cloned from cuttings. As noted by Christiaens et al. (2016), however, the optimal spectral power distribution for root development may be suboptimal for above-ground shoot growth, and vice versa.

US Patent Application Pub. No. 2018/0054974 discloses the use of near-infrared lighting to promote growth and production of various crop plants, where the leaves, stems, and flowers of the plants are exposed to a combination of photosynthetically active radiation and near-infrared radiation. However, much of the intelligence of plants is devoted to the behaviour of root tips in efficiently locating water and mineral resources in the soil, and so the root system benefits the most from effective intercellular communications. Near-infrared radiation results in increased production of nitric oxide by cytochrome c oxidase (Poyton et al. 2011), and near-infrared radiation penetrates more deeply into soil compared to visible light. Irradiating plant root systems with near-infrared radiation may therefore benefit plant health and growth.

Silva-Nava, J. et al., 2015, "D-Root: A System for Cultivating Plants with the Roots in Darkness or Under Different Light Conditions," *The Plant Journal* 84:244-255, disclosed an apparatus (Spanish patent ES 1091883Y) for irradiating plant root systems with LEDs or UV-B lamps independently of above-ground irradiance, but it is practical only for research purposes using controlled growth chambers. There is therefore a need for an apparatus that provides mostly independent control of above-ground and below-ground irradiation of plants.

Solid State Lighting

The advent of solid-state lighting, in particular the availability of high-flux semiconductor LEDs with narrow spectral bandwidths that span the photobiologically-active spectrum from approximately 280 nm to 800 nm and beyond, makes it possible to design and manufacture horticultural luminaires with precisely-controlled spectral power distributions. However, research to date has been either trial-and-error with no underlying hypothesis (e.g., Johkan, M., et al., 2012, "Effect of Green Light Wavelength and Intensity on Photomorphogenesis and Photosynthesis in *Lactuca sativa*," *Environmental and Experimental Botany* 75:128-133), or the reductionist approach of observing the effects of genome editing of single plant species such as *Arabidopsis*.

Companies such as Fluence Bioengineering (Austin, Tex.) and Lumigrow (Emeryville, Calif.) manufacture horticultural luminaires with variable spectral power distributions, which can be preset according to whether the horticulturalist or floriculturist is interested in propagating seedlings or cuttings, promoting vegetative growth, or flowering.

Similarly, companies such as Once Innovations (Plymouth, Minn.) manufacture livestock production luminaires for chicken, turkey and swine facilities, and aquaculture luminaires for fish farming Chickens, for example, may be exposed to red light during brooding to promote early growth and blue light for improved feed conversion ratios, improved bird behaviour, and other desired productivity goals (Delabbio, J. L. 2018. "The Science of Poultry Lighting," Plymouth, Minn.: Once Innovations Inc.).

SUMMARY

The present invention emulates changes in sky colour, sky colour distribution and sky irradiance to influence plant health, growth, and the production of flavonoids and other medicinally useful plant extracts through circadian and circannual rhythm entrainment. The invention also emulates changes in sky colour, colour distribution and irradiance to influence animal health and growth through circadian and circannual rhythm entrainment.

In order to promote the health and well-being of both plants and animals, the inventors have recognized a need for a biological luminaire and control system with a temporally and spatially varying spectral power distribution that can be optimized for specific plant species grown in greenhouse or vertical farm environments, or specific factory-raised animal species, such that the temporal and spatial changes in spectral power distribution serve to beneficially entrain their circadian and circannual rhythms or, for animals that live less than a year, their circadian and life cycle rhythms.

In a first embodiment, the invention includes a colour-changing luminaire with an associated controller that adjusts the spectral power distribution and photon or radiant flux output of the luminaire to emulate the colour and irradiance changes of daylight for the purpose of entraining circadian rhythms and either circannual or life cycle rhythms.

In a second embodiment, the invention includes at least two colour-changing luminaires with an associated controller that adjusts the spectral power distribution and photon or radiant flux output of the luminaires to emulate the spatial and temporal changes in daylight colour and irradiance for the purpose of entraining circadian rhythms and either circannual or life cycle rhythms.

In a third embodiment, the invention includes at least two colour-changing horticultural luminaires with an associated controller that adjusts the spectral power distribution and photon flux output to emulate the colour and irradiance changes of daylight for the purpose of entraining circadian rhythms and either circannual or life cycle rhythms and promoting plant health and growth, wherein at least one luminaire provides above-ground irradiation to the plant stems, shoots, leaves, and flowers, and at least one luminaire provides below-ground irradiation to the plant root system.

Disclosed herein is an illumination system comprising a luminaire having an adjustable spectral power distribution (SPD) and a controller that provides electrical power and control signals to the luminaire. The control signals automatically transition the SPD between a first SPD and a second SPD, wherein the transition corresponds to a change in light that entrains a biological rhythm in a life form.

Further disclosed is method for entraining a biological rhythm in a life form comprising the steps of: orienting a luminaire with an adjustable spectral power distribution (SPD) to illuminate the life form from above; connecting a controller to the luminaire so that the controller provides electrical power and control signals to the luminaire; and sending, automatically from the controller, control signals that transition the SPD between a first SPD and a second SPD; wherein the transition corresponds to a change in light that entrains a biological rhythm in the life form.

The disclosed and/or claimed subject matter is not limited by this summary, as additional aspects are presented by the following written description and associated drawings.

DETAILED DESCRIPTION

Glossary

Dawn—the period of time wherein the geometric centre of the sun is within 6 degrees above or 8 degrees below the horizon in the morning, for a given geographic location.

Dusk—the period of time wherein the geometric centre of the sun is within 6 degrees above or 8 degrees below the horizon in the evening, for a given geographic location.

R:FR—The ratio of red light to far-red light in a spectral power distribution

SPD—Spectral power distribution

Twilight—The soft, diffused light from the sky when the sun is below the horizon, either from daybreak to sunrise or, more commonly, from sunset to nightfall. In particular, twilight herein refers to the sky's spectral power distribution and irradiance when the sun is not visible above the horizon and its geometric centre is within 8 degrees below the horizon.

Exemplary System

Figure 1:
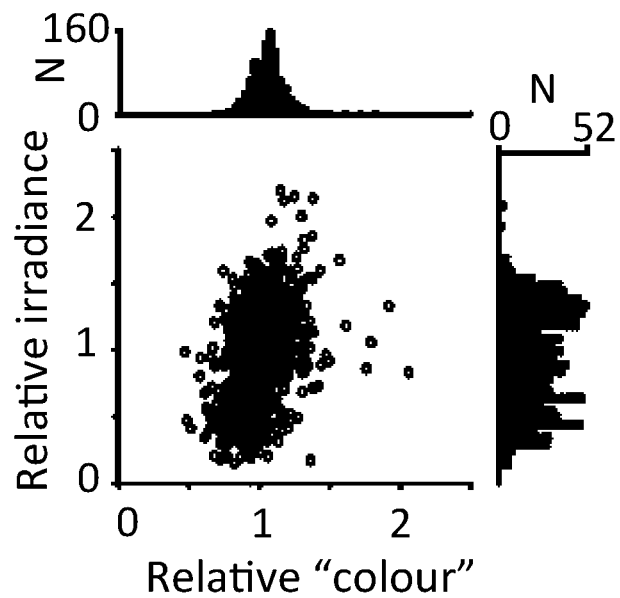
FIG. 1 is a prior art graph that shows daylight colour versus irradiance variability.
Figure 2:
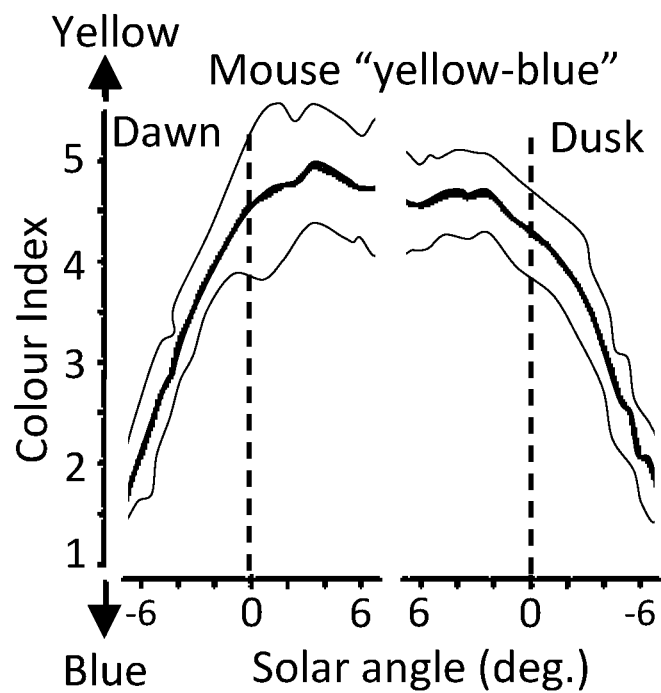
FIG. 2 is a prior art graph that shows the variation in yellow-blue daylight ratio at dawn and dusk.
Figure 3:
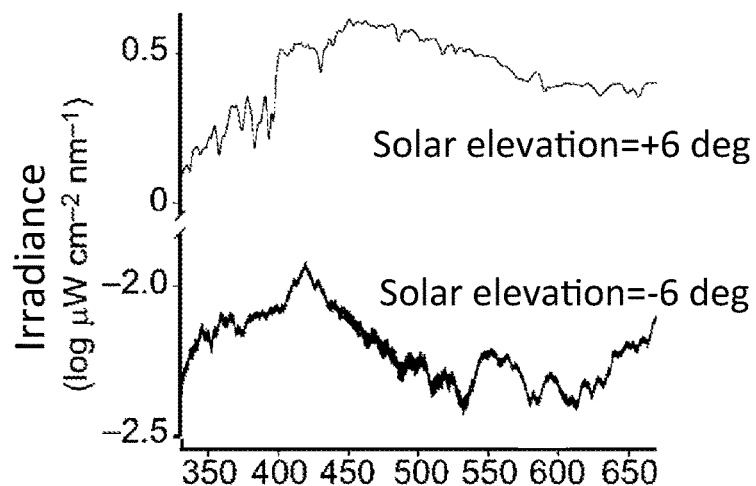
FIG. 3 is a prior art graph that shows daylight SPD before and after sunset.
Figure 4:
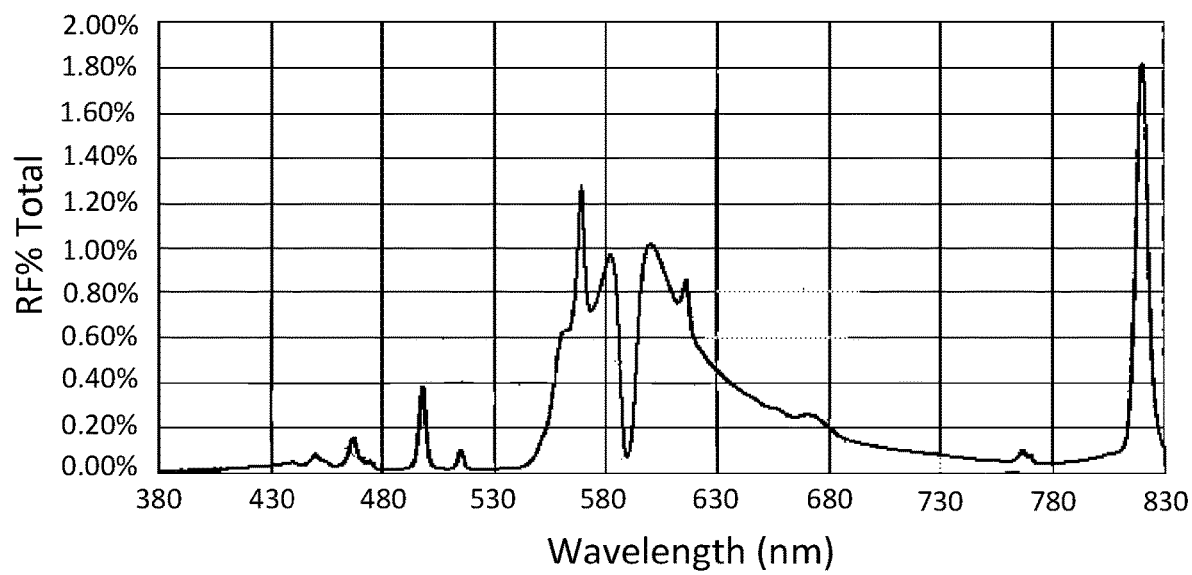
FIG. 4 is a prior art graph that shows the SPD of a typical high-pressure sodium (HPS) lamp commonly used for supplemental electric lighting in greenhouses and poultry farms.
Figure 5:
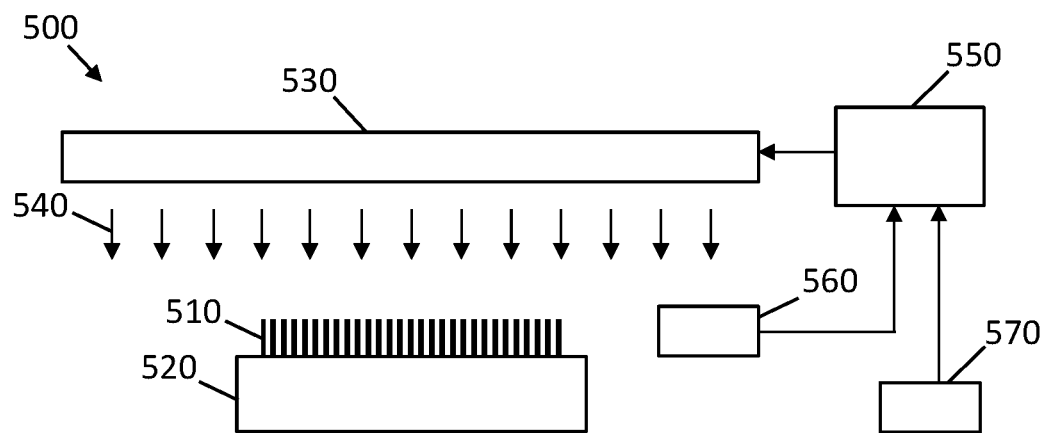
FIG. 5 shows a first embodiment of a plant illumination system that includes spectral and temporal control.

In FIG. 5, a plant illumination system 500 is shown for plants 510 growing in or from a substrate 520, wherein the substrate is soil or a support structure for hydroponic or aeroponic agriculture depending on the embodiment. The system 500 includes one or more horticultural luminaires 530 providing substantially directional or omnidirectional illumination 540 to the plants, and in some embodiments the substrate 520 forms part of the system. In this example, the light 540 from the luminaires 530 illuminates the plants 510 from above, providing the illumination at least in a vertical or downwards direction. The photon flux output and SPD of luminaires 530 are adjustable and are controlled by luminaire controller 550, which provides electrical power and control signals to the luminaires.

One or more sensors 560, such as for example a computer vision system or a chlorophyll fluorescence sensor (e.g., Lindqvist, J., et al., 2016, "Complexity of Chlorophyll Fluorescence Dynamic Response as an Indicator of Expressive Light Intensity," *IFAC-PapersOnline* 49-16:392-397) is employed in some embodiments to monitor plant status and provide feedback to controller 550. In some embodiments, one or more sensors 570, such as for example a quantum sensor, colorimeter, a soil temperature sensor, a soil moisture sensor, a soil acidity sensor, an air temperature sensor, a carbon dioxide concentration sensor, or an anemometer, is employed to monitor environmental conditions and provide feedback to controller 550. In designing control systems for horticultural, livestock production, and aquaculture lighting, it is useful to consider all possible circadian zeitgebers, including at least daylight colour and irradiance, and ambient temperature, and how the plants or animals might perform data fusion of the inputs in responding to them.

The controller 550 includes one or more interfaces via which the luminaires 530 are connected, and one or more interfaces via which the sensors 560, 570 are connected The controller has a processor, which may include multiple constituent processors, that is connected to the interfaces and to one or more computer-readable memories storing a program in the form of computer-readable instructions, which, when executed by the processor, cause the controller to automatically transition the SPD of the luminaires 530 from one SPD to another. The memory also stores computer-readable data, which is used by the processor to run the program. The data is created by the program, by an external program, or both. The data includes the times of sunset and sunrise for an optimal latitude for growth of the plants, desired SPDs for illumination from above, the side or omnidirectional SPD, SPD transitions, and durations of the SPD transitions, some or all of which entrain a biological rhythm of the plants. In some embodiments, the data includes the condition or status of the plants in response to the illumination that has been or is being provided to the plants.

In operation, controller 550 is programmed to control the photon flux output and SPD of luminaires 530 such that the illumination colour and irradiance changes at the beginning and end of the daily illumination period with the intent of optimally entraining the plants' circadian and circannual rhythms. The beginning of the daily illumination period corresponds, for example, to the start of dawn for the geographic location in which the plants are preferably grown, and the changes in illumination are made over the duration of this dawn. The end of the daily illumination period corresponds, for example, to the end of dusk for the geographic location in which the plants are preferably grown, and the changes in illumination are made over the duration of this dusk.

Controller 550 may optionally perform data fusion of the inputs from sensors 560 and 570 by first preconditioning the signals, as for example by temporal gating of a quantum sensor, and then performing data fusion operations that emulate the plant responses to environmental conditions. For example, if luminaires 530 provide supplemental electric illumination in a greenhouse, the controller may choose, on an overcast day, to augment the colour and irradiance changes perceived by the plants at sunrise or sunset such that it appears to the plants to be a clear day with a less ambiguous entrainment signal.

If there is no other lighting on the plants other than that provided by the luminaires 530, the output of the luminaires transitions between an SPD that alone emulates daylight and an SPD that alone emulates twilight. In particular, the output of the luminaires varies between an output that emulates the sky colour and irradiance when the geometric centre of the sun is 6 degrees above the horizon, and an output that emulates the sky colour and irradiance when the geometric centre of the sun is 8 degrees below the horizon (i.e., the luminaires emulate transitions spanning the "golden hour" and "blue hour"). Depending on the embodiment, the output of the luminaires varies gradually, in steps or abruptly, or varies between outputs that emulate the sky colour and irradiance for sun inclinations that are within than 6 degrees above to 8 degrees below the horizon for the particular geographic location or latitude of interest. However, if the luminaires 530 provide lighting in addition to natural lighting, the output of the luminaires transitions between an SPD that in combination with the natural lighting emulates daylight and an SPD that in combination with the natural lighting emulates twilight.

In one embodiment, the illumination colour changes emulate the changes that are observed in nature during twilight. In another embodiment, the illumination colour changes are chosen such that the plant photoreceptors optimally respond. It is known, for example, that phytochrome isoforms $P_r$ and $P_{fr}$ have specific peak spectral absorptances that differ from the SPD of natural illumination at and near twilight. Floriculturists sometimes use black shades at sunset to prevent the flowering crops from responding to changes in the R:FR ratio, but the same result can be achieved without mechanical shades by providing supplemental red or far-red lighting with quasimonochromatic LEDs with peak wavelengths close to the photoreceptor peak spectral absorptances to counteract or reinforce changes in the R:FR ratio at dusk. Similarly, supplemental red or blue lighting may be provided by the luminaires 530 at dawn to counteract or reinforce the responses to natural blue light. Supplemental red, far-red, and/or blue light may also be provided by the luminaires 530 before dawn or after dusk to advance or delay the plants' circadian clocks. The luminaires 530 in another embodiment further include near-infrared light-emitting diodes with peak wavelengths between approximately 800 nm and 1000 nm, and preferably near the spectral peak at 820 nm for cytochrome c oxidase activation. Such LEDs are activated at dawn to precondition the plant leaves, stems, shoots, and flowers against ultraviolet radiation damage from direct sunlight. (This applies even for indoor vertical farms, where it is becoming increasingly economical to provide ultraviolet radiation from UV-B and UV-A light-emitting diodes in order to promote the production of flavonoids and medicinal compounds.)

FIG. 5 may also represent a livestock production or aquaculture facility where luminaires 530 provide lighting for captive animals (not shown) and environmental sensors 570 such as, for example, air temperature sensors, provide input signals to controller 550, which is programmed to control the radiant output and SPD of luminaires 530 such that the illumination colour and irradiance changes at the beginning and end of the daily illumination period with the intent of optimally entraining the animals' circadian and circannual rhythms. Depending on the embodiment, substrate 520 may be omitted or may represent a barn floor or fish pond, for example Animals may reside in or on the substrate, at least part of the time.

Controller 550 may further be configured such the daily photoperiod is varied according to the seasons experienced by wild plants or animals. For plants and animals from temperate and arctic climates, the transition times at dawn and dusk can be similarly varied, being longer in winter months than summer months.

For the purposes of livestock production and facilities and aquaculture farms, the controller 550 may further provide excess blue light in its transition at dawn for animals with long-period circadian clocks, or excess red light or far-red in its transition at dusk for animals with short-period circadian clocks.

Figure 6:
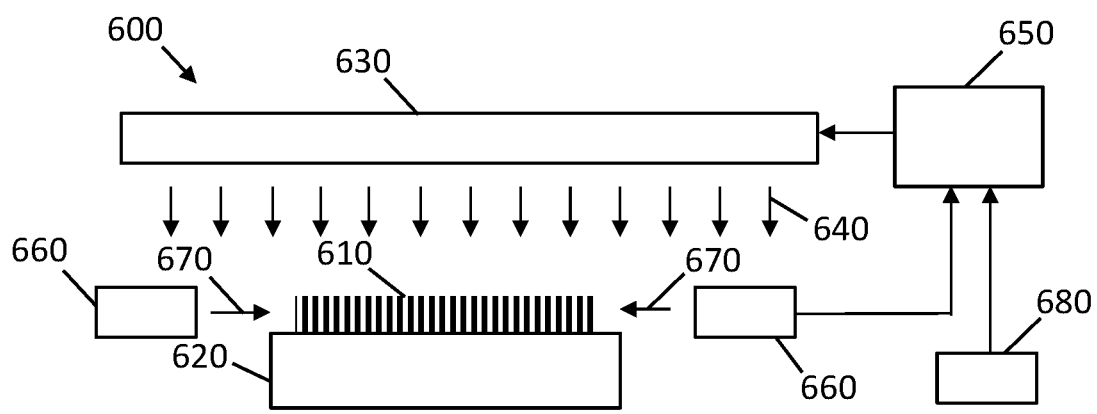
FIG. 6 shows a second embodiment of a plant illumination system that includes spectral, spatial, and temporal control.

FIG. 6 shows a plant illumination system 600 for plants 610 growing in or from a substrate 620. The system 600 includes one or more horticultural luminaires 630 providing substantially omnidirectional illumination 640 to the plants 610. As above, the substrate forms part of the system 600 in some embodiments. The photon flux output and SPD of luminaires 630 are adjustable and are controlled by luminaire controller 650, which provides electrical power and control signals to the luminaires. In addition, further horticultural luminaires 660 provide substantially directional illumination 670 that is also controlled by luminaire controller 650. The further luminaires 660 provide illumination in a sideways or horizontal direction to the plants 610. Further, one or more sensors 680, are employed in some embodiments to monitor plant status and environmental conditions and provide feedback to controller 650.

In operation, controller 650 is programmed to control the photon flux output and SPD of luminaires 630 and 660 such that the illumination colour changes at the beginning and end of the daily illumination period with the intent of optimally entraining the plants' circadian and circannual rhythms. The operation of controller 650 is the same as that of controller 550 in FIG. 5, with the addition that the photon flux outputs and SPDs of luminaires 630 and 660 may differ in order to emulate the temporal and spatial distributions of daylight colour (or SPD) and irradiance at dawn and dusk.

FIG. 6 may also represent a livestock production or aquaculture facility where luminaires 630 provide lighting for captive animals (not shown) and environmental sensors 680 such as, for example, air temperature sensors, provide input signals to controller 650, which is programmed to control the radiant output and SPD of luminaires 630, 660 such that the illumination colour and irradiance changes at the beginning and end of the daily illumination period with the intent of optimally entraining the animals' circadian and circannual rhythms. As above, the substrate 620 may be omitted or may represent a barn floor or fish pond, for example Animals may reside in or on the substrate, at least part of the time.

Figure 7:
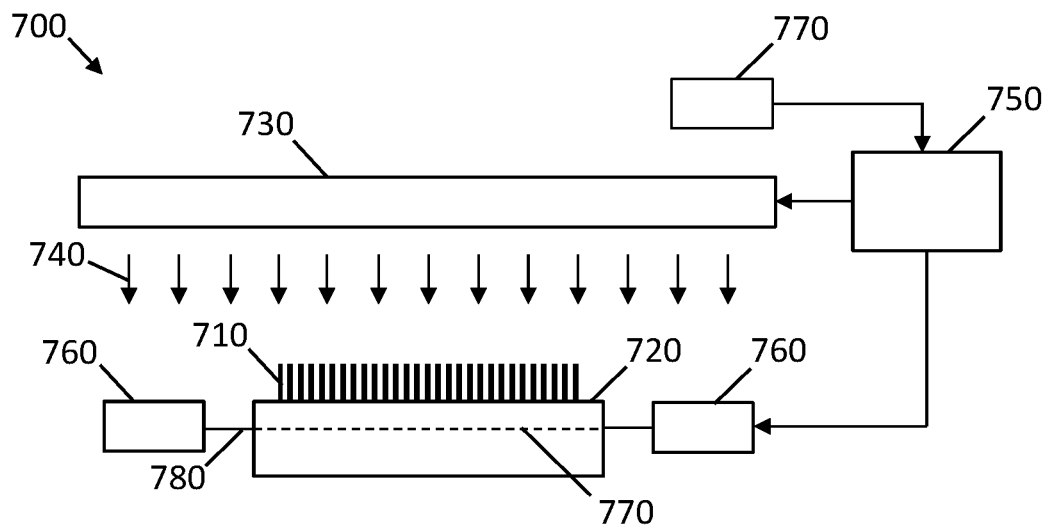
FIG. 7 shows a third embodiment of a plant illumination system that includes spectral, spatial, and temporal control.

FIG. 7 shows a plant illumination system 700 for plants 710 growing in or from a substrate 720. The system 700 includes the substrate 720, and one or more horticultural luminaires 730 providing substantially directional or omnidirectional illumination 740. In this example, the light 740 from the luminaires 730 illuminates the plants 710 from above, providing the illumination at least in a vertical or downwards direction. The photon flux output and SPD of luminaires 730 are adjustable and are controlled by luminaire controller 750, which provides electrical power and control signals to the luminaires. In addition, horticultural luminaires 760 provide illumination directly to the substrate 720 and have a photon flux output and SPD that are also controlled by luminaire controller 750.

For soil substrates, the illumination from horticultural luminaires 760 may be provided, for example, by a fiber-optic mesh 770 embedded in the substrate, wherein the fiber-optic strands are designed to emit light along their length. Light from the luminaires 760 is directed into the mesh 770 by relatively lossless optic fibers 780 or other light guides. An example of such a fiber optic is disclosed in Shustack, P. J. et al., 2014, "Photocuring in Areas Where You Typically Cannot Get Light," Proc. UV+EB Technology Expo and Conference 2014.

For hydroponic and aeroponic applications, the horticultural luminaires 760 may illuminate a fiber-optic mesh 770, or they may directly illuminate the plant roots through a transparent growth medium in or forming part of the substrate 720.

In operation, controller 750 is programmed to control the photon flux output and SPD of luminaires 730 such that the illumination colour and irradiance changes at the beginning and end of the daily illumination period with the intent of optimally entraining the plants' circadian and circannual rhythms. Controller 750 may also be programmed to control the photon flux output and SPD of luminaires 760 such that optimal root system development and plant health is obtained.

Plant roots may exhibit positive phototropism for red light and negative phototropism for blue light, presumably to ensure that the roots grow downwards toward soil resources than towards the surface. One or more horizontal layers of fiber-optic mesh, each with its own luminaire 760 providing independently-controlled SPDs, may be employed in order to direct root growth and development as desired as the roots grow towards and through the meshes.

The operation of controller 750 is the same as that of controller 550 in FIG. 5 or controller 650 in FIG. 6, with the addition that the photon flux outputs and SPDs of luminaires 730 and 760 may differ in order to optimize root system growth independently of the above-ground plant leaves, stems, shoots, and flowers.

Plant Optimization Method

Figure 8:
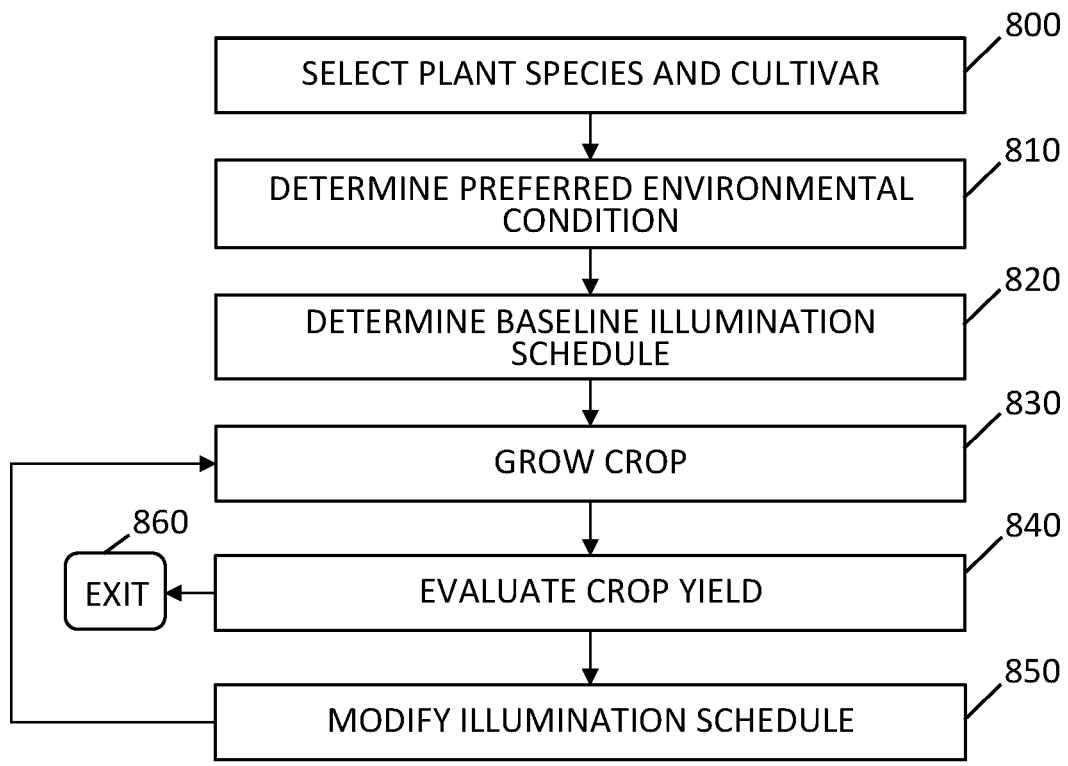
FIG. 8 shows a flowchart for the optimization of temporally- and spatially-varying SPD for optimal plant health and growth, according to an embodiment of the present invention.

FIG. 8 illustrates an example of the method wherein the scheduling of the photon flux output and SPD of the luminaires is optimized for plant health, growth, and the production of flavonoids and other medicinally useful plant extracts on a per-species basis.

In Step 800, a plant species is selected. It is known that different cultivars of the same plant species may have different environmental requirements, and so a particular cultivar may also have to be selected.

In Step 810, the plant's preferred environmental conditions are determined, including geographic latitude, daily light integral and shade requirements, temperature range, soil type, moisture content, mineral nutrients, and so forth as may be present in the wild state of the selected plant species.

In Step 820, a baseline illumination schedule is determined based on the selected plant's preferred geographic latitude and climatic data. The baseline illumination schedule is intended for predetermined growth goals of the plants to be reached. For example, if a leafy green vegetable such as lettuce is known to thrive outdoors in a given geographic region, a Typical Meteorological Year (TMY) weather file that is representative of the region may be selected. The data contained in this weather file can be used to determine sunrise and sunset, hourly temperature, rainfall, and solar irradiance on a daily basis. This data can be used as a basis for determining the baseline illumination schedule, even if the crops are to be grown in a greenhouse in a different geographic region, or indoors in a plant factory. In a greenhouse environment, supplemental electric lighting or motorized shading devices may be employed as required.

In many situations, the maximum photon flux density incident upon the plant leaf canopy will be less than what the plants would experience outdoors under clear skies. Rather than dimming the horticultural luminaires to emulate hourly cloud cover conditions, therefore, it is more likely that the plants will be exposed to constant illumination sufficient to meet their daily light integral requirements.

Critical to the baseline illumination schedule are the sunrise and sunset times, a period of roughly one-half hour wherein the horticultural luminaires are dimmed from constant daytime illumination to nighttime. During these periods, the SPD is changed to emulate the transition in colour from daytime to twilight conditions, and vice versa.

Data representing the desired or optimum daytime SPD, the desired or optimum twilight SPD, the durations of each, the duration of the transitions between each, and the changes in SPD during the transitions are stored in the luminaire controller as the baseline illumination schedule.

In Step 830, a crop is grown while being subjected to illumination from the luminaires in accordance with the illumination schedule.

In Step 840, the crop yield is evaluated in accordance with the predetermined goals of plant health, growth, flowering, fruit or vegetable quality, and the production of flavonoids, terpenes, medicinally useful plant extracts and other crop-specific criteria. If the goals are not satisfied, the illumination schedule may be varied (Step 850) and Steps 830 and 840 repeated. If the crop is satisfactory, the process ends at Step 860.

Animal Optimization Method

Figure 9:
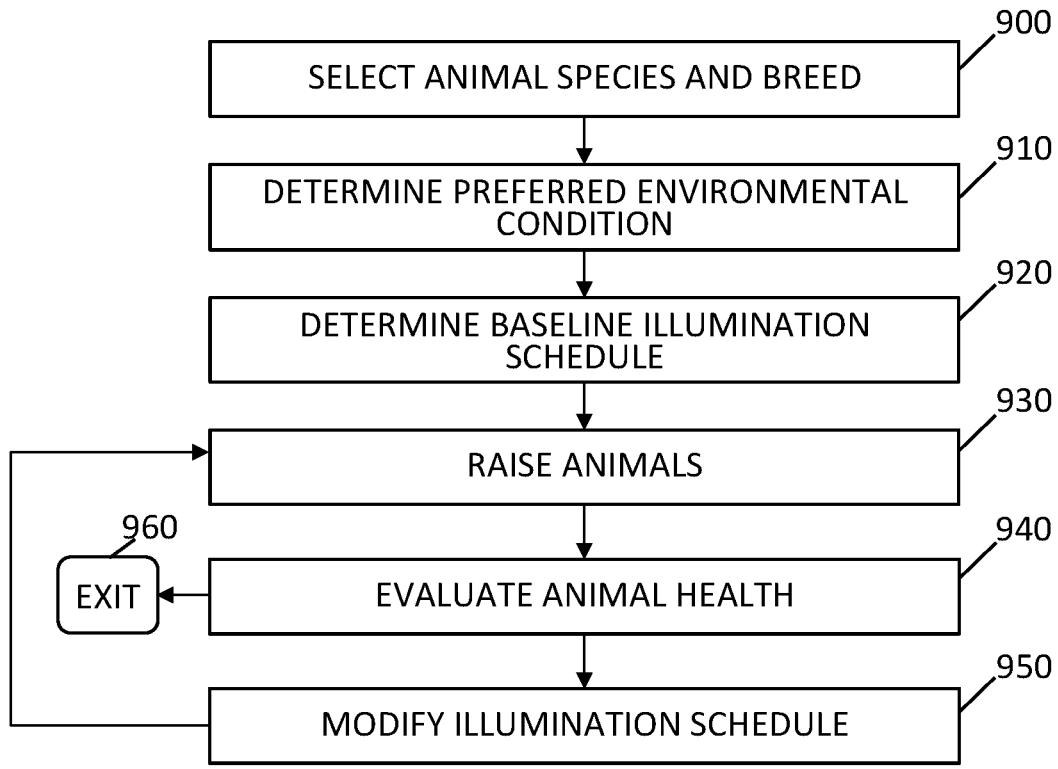
FIG. 9 shows a flowchart for the optimization of temporally- and spatially-varying SPD for optimal animal health and growth, according to an embodiment of the present invention.

FIG. 9 illustrates an example of the method wherein the scheduling of the radiant flux output and SPD of the luminaires is optimized for animal health, behaviour, and growth on a per-species and per-breed basis.

In Step 900, an animal species is selected. It is known that different breeds of the same animal species may have different environmental requirements, and so a particular breed may also have to be selected.

In Step 910, the animal's preferred environmental conditions are determined.

In Step 920, a baseline illumination schedule for the selected breed is determined based on past industry experience with domestic animals or wildlife observations, where the illumination schedule is intended for the animals selected breed to attain predetermined growth goals.

Critical to the baseline illumination schedule are the sunrise and sunset times, a period of roughly one-half hour wherein the livestock production or aquaculture luminaires are dimmed from constant daytime illumination to nighttime. During these periods, the SPD is changed to emulate the transition in colour from daytime to twilight conditions, and vice versa.

Data representing the desired or optimum daytime SPD, the desired or optimum twilight SPD, the durations of each, the duration of the transitions between each, and the changes in SPD during the transitions are stored in the luminaire controller as the baseline illumination schedule.

In Step 930, the animals are raised while being subjected to illumination from the luminaires in accordance with the illumination schedule.

In Step 940, the animals' health, behaviour, and marketability is evaluated in accordance with the predetermined goals. If the goals are not satisfied, the illumination schedule may be varied (Step 950) and Steps 930 and 940 repeated. If the goals have been satisfied, the process ends at Step 960.

Figure 10:
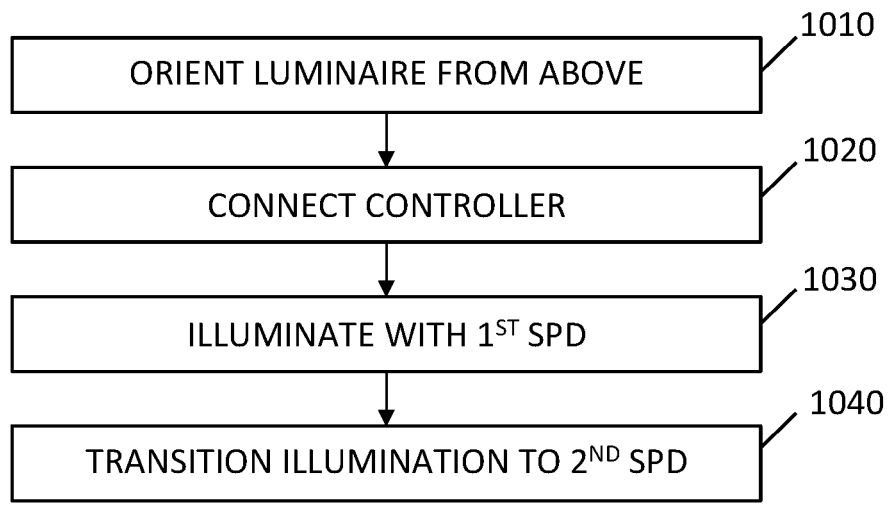
FIG. 10 is a flowchart of a process for transitioning the SPD, according to an embodiment of the present invention.

Referring to FIG. 10, a flowchart of an exemplary process is seen for the operation of a system 500. In Step 1010, the luminaires 530 are oriented above the plants, so that they provide illumination at least in a downwards direction onto the plants. In Step 1020, the luminaires are connected to the luminaire controller 550. In Step 1030, the luminaires illuminate the plants with a first SPD, for example an SPD that emulates daylight. In Step 1040, the controller sends signals to the luminaires so that the illumination that they are providing transitions from the first SPD to a second SPD, for example an SPD that emulates twilight. This process is also applicable to the system 700 for controlling luminaires 730. A similar process can be used to control the luminaires 760.

Figure 11:
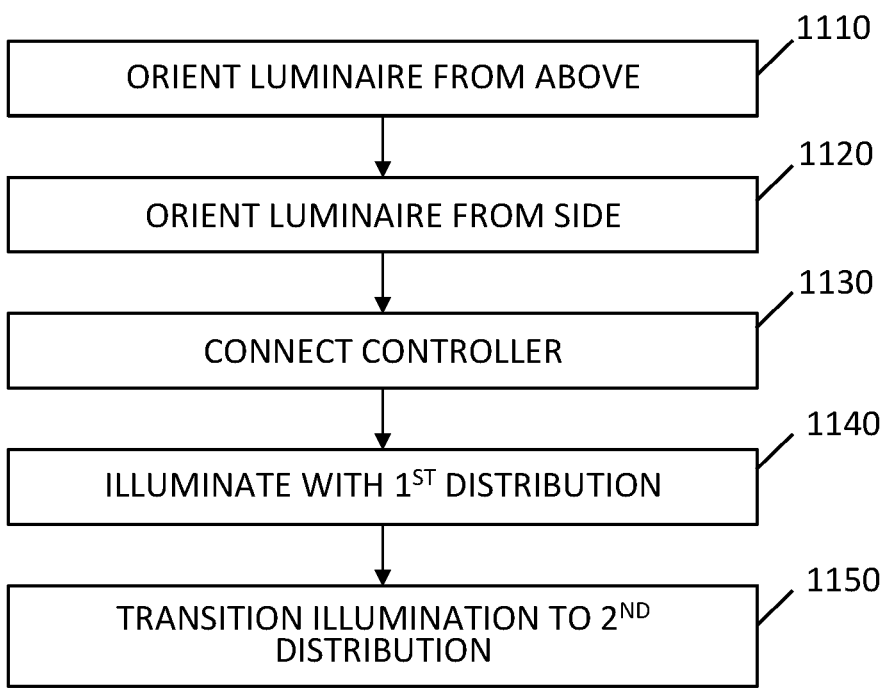
FIG. 11 is a flowchart of a process for transitioning the distribution of illumination, according to an embodiment of the present invention.

Referring to FIG. 11, a flowchart of an exemplary process is seen for the operation of a system 600. In Step 1110, the luminaires 630 are oriented above the plants, so that they provide illumination at least in a downwards direction onto the plants. Step 1120, further luminaires 660 are oriented to the side of the plants, so that they provide illumination at least in a sideways direction onto the plants. In Step 1130, the luminaires are connected to the luminaire controller 650. In Step 1140, the luminaires illuminate the plants with an SPD having a first spatial distribution, for example a spatially varying SPD that emulates daylight. In Step 1150, the controller sends signals to the luminaires so that the illumination that they are providing transitions from the first spatial distribution to a second spatial distribution, for example a spatially varying SPD that emulates twilight.

In both plant and animal optimization methods, the quantity of data that must be evaluated to determine crop yield or animal health, particularly if the number of input signals from the sensors results in a multidimensional optimization problem for data fusion, may be confusing if not overwhelming. In such situations, it may be necessary to employ artificial intelligence techniques using deep learning architectures to discover hidden patterns that inform changes to the illumination schedule.

The configurations and/or approaches described herein are exemplary in nature, and specific implementations or examples are not to be considered in a limiting sense, because numerous variations are possible. The specific methods or processes described herein may represent one or more of any number of processing strategies. As such, various acts illustrated may be performed in the sequence illustrated, in other sequences, in parallel, or in some cases omitted. Likewise, the order of the above-described processes may be changed. The subject matter of the present disclosure includes all novel and nonobvious combinations and subcombinations of the various methods, processes, systems and configurations, and other features, functions, acts, and/or properties disclosed herein, as well as any and all equivalents thereof.

The embodiments of the invention may be varied in many ways. Such variations are not to be regarded as a departure from the scope of the invention, and all such modifications as would be obvious to one skilled in the art are intended to be included within the scope of the claims.

The invention claimed is:

1. A method for directing growth of a plant's roots comprising:
   providing a growth medium in which the roots grow;
   connecting a controller to a luminaire that has an adjustable spectral power distribution (SPD) and an adjustable photon flux output;
   connecting the controller to a further luminaire that has an adjustable SPD and an adjustable photon flux output;
   providing electrical power and control signals from the controller to the luminaire to control its SPD and its photon flux output;
   providing further electrical power and further control signals from the controller to the further luminaire to control its SPD and its photon flux output;
   directing light from the luminaire via the growth medium to the roots; and
   directing further light, from the further luminaire, via the growth medium to the roots;
   wherein the light and the further light direct growth of the roots.

2. The method of claim 1, wherein the growth medium is a substrate or is transparent, or is a transparent substrate.

3. The method of claim 1, wherein the growth medium is soil or a support structure for hydroponic or aeroponic agriculture.

4. The method of claim 1, wherein the light from the luminaire is directed into the growth medium via a fiber-optic mesh.

5. The method of claim 4, comprising arranging the fiber-optic mesh horizontally in the growth medium.

6. The method of claim 1, comprising controlling the SPDs of the luminaire and the further luminaire independently.

7. The method of claim 1, wherein:
the light from the luminaire is directed into the growth medium via a fiber-optic mesh; and
the further light, from the further luminaire, is directed into the growth medium via a further fiber-optic mesh.

8. The method of claim 7, wherein the growth of the roots is directed towards and through the fiber-optic mesh and the further fiber-optic mesh.

9. The method of claim 7, wherein:
the light comprises red light, far-red light, near-infrared light or any combination selected therefrom; and
the further light comprises blue light, ultraviolet light or both blue light and ultraviolet light.

10. A method for controlling growth of a plant comprising:
providing a growth medium in which roots of the plant grow;
illuminating the growth medium with light from a luminaire;
orienting a further luminaire to deliver further light to a canopy of the plant, the further luminaire having an adjustable spectral power distribution (SPD) and an adjustable photon flux output;
connecting a controller to provide electrical power to the luminaire, and further electrical power and control signals to the further luminaire; and
transitioning, via the control signals, the SPD gradually between a first SPD and a second SPD twice per day while adjusting the photon flux output;
wherein the transitions in the SPD and the adjustments to the photon flux output correspond to changes in illumination that entrain a biological rhythm in the plant;
wherein the light is provided via the growth medium to the roots and directs growth of the roots.

11. The method of claim 10, wherein the growth medium is a substrate or is transparent, or is a transparent substrate.

12. The method of claim 10, wherein the growth medium is soil or a support structure for hydroponic or aeroponic agriculture.

13. The method of claim 10, comprising controlling the luminaire and the further luminaire independently.

14. The method of claim 10, wherein the further luminaire's SPD transitions between the first SPD and the second SPD over a period of half an hour.

15. The method of claim 10, wherein:
the SPD is transitioned at times of and during periods of sunrise and sunset; and
the transitions further entrain a circannual or lifecycle rhythm in the plant.

16. The method of claim 10, wherein the transitions emulate changes of a sky color and a sky irradiance between when a geometric center of the sun is 6 degrees above a horizon and when the geometric center of the sun is 8 degrees below the horizon.

17. The method of claim 10, wherein the light from the luminaire is directed into the growth medium via a fiber-optic mesh.

18. The method of claim 17, comprising arranging the fiber-optic mesh horizontally in the growth medium.

19. The method of claim 17, wherein the growth of the roots is directed towards and through the fiber-optic mesh.

* * * * *